United States Patent [19]

Wong et al.

[11] Patent Number: 4,698,312

[45] Date of Patent: Oct. 6, 1987

[54] STABILIZING BLOOD CELLS WITH AROMATIC POLYALDEHYDE FOR USE IN HEMATOLOGY CONTROLS AND CALIBRATORS

[75] Inventors: Show-Chu Wong, West Nyack; Harbans S. Deol, Walden; Debra L. Harz, Spring Valley, all of N.Y.

[73] Assignee: Fisher Scientific Company, Pittsburgh, Pa.

[21] Appl. No.: 889,748

[22] Filed: Jul. 28, 1986

[51] Int. Cl.[4] ............................................. G01N 31/00
[52] U.S. Cl. ......................................... 436/10; 424/3; 436/16
[58] Field of Search ........................................ 436/8–19, 436/519–521; 424/3

[56] References Cited

U.S. PATENT DOCUMENTS

| | | | |
|---|---|---|---|
| 3,708,572 | 1/1973 | Peetoom et al. | 436/10 |
| 3,714,345 | 1/1973 | Hirata | 424/3 |
| 3,715,427 | 2/1973 | Hirata | 424/3 |
| 4,287,087 | 9/1981 | Brinkhous et al. | 436/10 |
| 4,390,632 | 6/1983 | Carter | 436/10 |

Primary Examiner—Deborah L. Kyle
Assistant Examiner—T. J. Wallen
Attorney, Agent, or Firm—Alan M. Doernberg

[57] ABSTRACT

Blood cells such as erythrocytes of animal origin are treated with a solution containing water, an organic cosolvent (such as dimethylsulfoxide, alone or admixed with a polyol), an aromatic polyaldehyde (such as phthaldialdehyde) and optionally salts and buffers. In an illustrative case, the treating solution is hypertonic and shrinks goat erythrocytes to the size of human platelets.

20 Claims, No Drawings

STABILIZING BLOOD CELLS WITH AROMATIC POLYALDEHYDE FOR USE IN HEMATOLOGY CONTROLS AND CALIBRATORS

The present invention relates to hemotology control and calibrator components prepared by aldehyde treatment (fixing) of blood cells such as erythrocytes of animal origin.

Aldehydes have been used for many years to fix or stabilize blood cells, and especially erythrocytes of animal origin, for use in hematology controls. For example, avian erythrocytes are swelled and fixed in U.S. Pat. No. 3,640,896 to Di Casperis for use as human white blood cell analogs; goat erythrocytes are shrunken and then fixed in U.S. Pat. No. 4,179,398 to Hunt for use as human platelet analogs. In U.S. Pat. No. 4,436,821, the cells are partially fixed before being shrunken. See also U.S. Pat. No. 4,579,824 to Louderback et al.

In these patents and other literature, various aliphatic monovalent aldehydes (formaldehyde, acetaldehyde) and glutaraldehyde (an aliphatic divalent aldehyde) are used. Commonly, a polyol is present during the treatment, in a post-treatment or in the suspending medium for the fixed cells in use for a variety of purposes: e.g., for freeze stability (U.S. Pat. No. 4,199,471), to affect osmotic pressure (U.S. Pat. No. 4,436,821) and to prevent cell-to-cell crosslinking (U.S. Pat. No. 4,390,632). Organic solvents are otherwise generally not used during or after the aldehyde treatment, except that U.S. Pat. No. 4,302,355 to Turner, et al does employ dimethylsulfoxide (DMSO) at a concentration of 2.5–20% (v/v) in saline to resuspend platelets which have been previously fixed with dichromate and glutaraldehyde. See also col. 4 of U.S. Pat. No. 4,436,821.

BRIEF DESCRIPTION OF THE INVENTION

The present invention employs aromatic polyaldehydes such as phthaldialdehyde to fix or stabilize blood cells for use as components in hematology controls and calibrators. Thus the present invention provides a method for preparing a stabilized cell component of a hematology control or calibrator by reacting blood cells with an aqueous aldehyde solution, characterized by the aqueous aldehyde solution comprising:

(a) water, (b) an aromatic polyaldehyde having carbonyls attached to aromatic ring carbons, and (c) an organic co-solvent in an amount miscible with water and sufficient to solubilize the aromatic polyaldehyde in the mixture.

The present invention further provides a hematology control component comprising an aqueous suspension of blood cells which have been stabilized with an aromatic polyaldehyde having carbonyls attached to aromatic ring carbons.

DETAILED DESCRIPTION OF THE INVENTION

In preparing components of hematology controls and calibrators from blood cells, treatments are employed to impart three characteristecs: stability, a desired degree of rigidity and a desired cell volume (such as the mean cell volume or MCV value). Previously, aldehydes have been used to impart stability to components used to simulate red cells or to simulate platelets and have been used to impart rigidity (and resistance to lysing) to components used to simulate white cells. In those instances in which a change of cell volume is a desired feature of the preparation process (U.S. Pat. Nos. 4,179,398, 4,436,821 and 4,579,824) two approaches have been taken. In the first approach, cell size has been adjusted with hypotonic (hypo-osmotic) or hypertonic (hyper-osmotic) solutions before aldehyde treatment; in the second approach, the cells are treated lightly (stabilized, but not fixed) with aldehyde and then shrunk in hypotonic suspending media or expanded in hypertonic suspending media. In neither approach is the osmality of the aldehyde solution adjusted; and, in the second approach, the aldehyde treating step is kept intentionally short to avoid the cells becoming too rigid for subsequent size adjustment. Representative aldehyde treating solutions in these references comprises mixtures of a small volume of aqueous aldehyde (e.g., 40 ml of 37% formaldehyde) with large volumes of physiological saline (e.g., 500 ml of 0.9% NaCl) to assure osmality near 300 mOsm/kg.

By contrast, the present invention employs an aqueous aldehyde solution with an aromatic polyaldehyde and an organic co-solvent. Such a solution can, itself, be adjusted as to osmality so as to suspend the cells in the aldehyde solution and obtain both stabilization and size adjustment. Even with exposures of 18 hours at 25° C. with such solutions (see Example 1, below) the cells do not become too rigid to be lysed. Conversely, the same aqueous/organic solution of aromatic polyaldehyde can be used with higher temperature exposure or longer fixing time to fix cells for simulation of white cells (i.e., cells resistant to lysing).

The aromatic polyaldeyde should be a compound having at least two carbonyls (—CH=O) attached to the ring atoms of aromatic rings. Examples include 1,2-benzenedialdehyde (phthaldialdehyde), 1,3-benzenedialdeyde, 1,3,5-benzenetrialdehyde, 1,2-napthalenedialehyde, 1,4-napthalene-dialdehyde and 9,10-anthracenedialdehyde. Preferred are the dialdehydehydes with carbonyls attached to adjacent ring carbons, and especially phthaldialdehyde.

The remainder of the solution contains water and at least one organic co-solvent, and may also contain salts (e.g., NaCl) and buffers (e.g., sodium phosphates). Preferably, the organic solvent is a mixture of dimethylsulfoxide (or another water-miscible organic cosolvent which can solubilize the dialdehyde) with a polyol (e.g., glycerol). Alternatively, a single solvent (e.g., dimethylsulfoxide) can be used. A representation mixture is:

| O—phthaldialdehyde | 20 g/l |
| --- | --- |
| DMSO | 100 ml/l |
| Glycerol | 100 ml/l |
| PBS | 800 ml/l | where the PBS used has the desired base osmality and pH, such as:

| NaCl | 7.65 g/l |
| --- | --- |
| Na$_2$HPO$_4$ | 0.72 g/l |
| NaH$_2$PO$_4$ | 0.21 g/l | which has a base osmality of 260±5 mOsm/kg and a pH of 7.2±0.1. The base osmality of the PBS is probably raised by the addition of the aldehyde, DMSO and glycerol, but the overall solution (PBS, DMSO, glycerol and aldehyde) is believed to be highly hypertonic (osmality more than 290 mOsm/kg). Adjustments in the osmality of the overall solution can most easily be made by lowering the NaCl content of the aqueous component and maintaining the concentration of the other components constant.

Various types of human and animal cells can be treated with the aromatic aldehyde solution. Examples and preferred cases are tabulated below:

| Cell source | Treatment | To Simulate Human |
| --- | --- | --- |
| Avian erythrocytes | Swell and fix | white cells |
| Human erythrocytes | Stabilize | red cells |
| Goat erythrocytes | Shrink and Stabilize | platelets |
| Human platelets | Stabilize | platelets |
| Bovine erythocytes | Stabilize | red cells |
| Human leukocytes | Stabilize | white cells |

In those instances where no shrinking or swelling is desired, the overall formulation should have an osmality near 300 mOsm/kg. In those instances where shrinking is desired, the osmality of the aldehyde solution should be higher. In those instances where swelling is desired, the osmality of the aldehyde solution should be lower.

For a particular fixative formulation and cells being treated, the final cell size can differ with different fixing times and temperatures. In some cases, the cells initially swell and then shrink back to or below their initial size.

In those instance where stabilization (not fixing) is desired, treatment conditions should remain below 30° C. if reaction times over about 10 minutes are employed. With lower temperatures (e.g., 4°-20° C.), longer reaction times (e.g., up to 15 hours) are suitable. With higher temperatures (e.g., 25°-37° C.), short reaction times (e.g., 1-5 minutes) are preferred. In time course experiments, it has been found that, in hypertonic media, the cells (especially goat erythrocytes) shrink to their minimum volume (for the experiment) in the first half hour, with aldehyde reaction continuing noticeably for several hours (at 24° C., some effect is seen up to 18 hours). Once the cells are washed and resuspended in isotonic media, cells treated for a shorter period swell back to an intermediate cell volume (between their initial cell volume and the minimum cell volume), while cells treated for longer periods swell back less, if at all.

For example, goat cells of MPV 12.1 shrank to 9.2 MPV in the first few minutes and 8.5 in one-half hour, but swelled back to 10.0 after washing in both cases. Other goat cells of MPV 15 shrank to 8.8 overnight in the reaction and after resuspension had an MPV of 9.2. Another batch with MPV 15.1 was treated for 7.5, 18 and 42 hours in accordance with Example 1 at room temperature, to give final MPV values after washing of 9.6, 9.0 and 9.0, respectively. These values were relatively stable up to 90 days in a hematology control formulation.

The same effect was seen comparing one hour treatment at 37° C. versus overnight treatment at 37° C., less swell-back in the latter case. Therefore longer treatment can be used as an additional variable to achieve desired cell volume of the treated cells. In similar fashion, reducing the aldehyde concentration can cause reduced rigidification (over the same treatment period) so that the cells will swell back more.

The process generally starts with washed cells separated from other types of cells (e.g., goat erythrocytes from which goat white cells and platelets have been removed by centrifigation and separation). The cells are suspended in the complete aqueous/organic aromatic aldehyde solution which is either at the treatment temperature (especially if it is 25° C. or below) or is thereafter brought to the treatment temperature (especially if it is elevated, e.g., 37° C., for fixing). The reaction mixture can be kept at a single treatment temperature for the treatment period or the temperature can be adjusted one or more times during the treatment period.

At the conclusion of the treatment period, the treated cells should be drained of treating solution, washed and resuspended. Instead of resuspending in the overall hematology control formulation, the treated cells are normally resuspended in isotonic media for storage (typicaly at a temperature less than 10° C., e.g., 2°-8° C.). Treated cells can be taken from storage as desired for formulation of a multicell control or for dilution in a single cell control or calibrator. Desirably, the size and lysing characteristics of an aliquot of the stored treated cells (after a representative dilution) are checked before such use.

EXAMPLE 1

Stabilizing Goat Erythrocytes

PBS was prepared from deionized water and the following salts:

| | |
| --- | --- |
| NaCl | 7.65 g/l |
| $Na_2HPO_4$ | 0.72 g/l |
| $NaH_2PO_4$ | 0.21 g/l | and sterile filtered with a 0.2 micron filter.

Such PBS has a pH of 7.2±0.1 and an osmality of 260±5 mOsm/kg. In a glass container, the following components (per liter of final solution) were mixed:

| | |
| --- | --- |
| O—phthaldialdehyde | 20 g/l |
| DMSO | 100 ml/l |
| Glycerol | 100 ml/l |
| PBS | 800 ml/l | by adding the ingredients in the indicated order and mixing well during each addition (the DMSO should dissolve the phthaldialdehyde before the glycerol is added). The solution was then filtered through filter paper.

Fresh goat blood was centrifuged in one liter bottles at room temperature, and the plasma and buffy coat were siphoned off and discarded. The cells in each bottle were resuspended in 300 ml PBS and the suspended cells passed through sterile polyester fibers into one liter centrifuged bottles. The bottles were filled with PBS to three-quarters full. Centrifugation and siphoning off were then repeated, the cells were resuspended in 700 ml PBS and centrifugation and siphoning off repeated again. The volume of washed cells was then estimated and twice the volume of PBS added (e.g., 50 ml of cell resuspended in 100 ml PBS). The resuspended washed cells were then transferred to a glass vessel equipped with a stir bar. An equal volume (e.g., 150 ml) of the above aqueous/organic aldehyde solution was then added under constant stirring, which was maintained at 24° C.±2° C. overnight (15 to 18 hours).

The cells were than resuspended in PBS, transfered to one liter bottles and centrifuged. Each bottle was rotated on its side to cut off (resuspend) any lightly fixed cells and the supernatant was then decanted off. The treated cells were then resuspended in 700 ml PBS with vigorous shaking, rotated, then supernatant decanted off, and the cells resuspended and centrifuged. The cells were then resuspended in twice their volume of PBS and 2% bovine serum albumin (BSA) added at a volume ratio of 1 ml 30% BSA: 20 ml fixed diluted cells. The BSA-suspended cells were then kept at 4° C.±2° C. for at least 18 hours and up to 4 days.

The BSA-suspended cells were then resuspended in PBS (¾ full), centrifuged and rotated and the supernatant poured off. The cells were then resuspended in PBS and filtered through a coarse sintered glass funnel under low vacuum. The filtered treated cells were stored at 2°-8° C. Before each use, the stored cells were checked for sterility and also checked for lysability by diluting 1:10 or 1:20 and then injected into a Coulter S+II hematology instrument. The cells showed no tail below 50 MCV units (femptoliters) in the white cell measurement (i.e., cells which survived lysing intact).

We claim:

1. A method for preparing a stabilized cell component of a hematology control or calibrator by reacting blood cells with an aqueous aldehyde solution, characterized by the aqueous aldehyde solution comprising:
   (a) water,
   (b) an aromatic polyaldehyde having carbonyls attached to aromatic ring carbons, and
   (c) an organic co-solvent in an amount miscible with water and sufficient to solubilize the aromatic polyaldehyde.

2. The method of claim 1 wherein the aromatic polyaldehyde is a dialdehyde with two carbonyls attached to adjacent aromatic ring carbons.

3. The method of claim 2 wherein the aromatic polyaldehyde is phthaldialdehyde.

4. The method of claim 3 wherein the blood cells reacted with the aromatic polyaldehyde are goat erythrocytes and the fixed cell component is a platelet analog.

5. The method of claim 4 wherein the aqueous aldehyde solution is sufficiently hypertonic to shrink the goat erythrocytes to substantially the size of human platelets.

6. The method of claim 1 wherein the blood cells reacted with the aromatic polyaldehyde are goat erythrocytes and the fixed cell component is a platelet analog.

7. The method of claim 6 wherein the aqueous aldehyde solution is sufficiently hypertonic to shrink the goat erythrocytes to substantially the size of human platelets.

8. The method of claim 1 wherein the aqueous aldehyde solution is sufficiently hypertonic to shrink the blood cells to substantially the size of human platelets.

9. The method of claim 1 wherein the aqueous aldehyde solution is sufficiently hypotonic to swell the blood cells to substantially the size of human white blood cells.

10. The method of claim 9 wherein the blood cells are avian erythrocytes.

11. The method of claim 9 wherein the blood cells are human erythrocytes.

12. The method of claim 1 wherein the organic cosolvent is dimethylsulfoxide.

13. The method of claim 1 wherein the co-solvent is a mixture of dimethylsulfoxide with a watersoluble polyol of 2-8 carbons.

14. The method of claim 13 wherein the watersoluble polyol is glycerol.

15. A hemotology control component comprising an aqueous suspension of blood cells which have been stabilized with an aromatic polyaldehyde having carbonyls attached to aromatic ring carbons.

16. The hematology control component of claim 15 wherein the aromatic polyaldehyde is a dialdehyde with two carbonyls attached to adjacent aromatic ring carbons.

17. The hematology control component of claim 16 wherein the aromatic polyaldehyde is phthaldialdehyde.

18. The hematology control component of claim 17 wherein the blood cells are goat erythrocytes shrunken to substantially the size of human platelets.

19. The hematology control component of claim 17 wherein the blood cells are avian erythrocytes swelled to substantially the size of human white blood cells.

20. The hematology control component of claim 15 wherein the blood cells are avian erythrocytes swelled to substantially the size of human white blood cells.

* * * * *